(12) United States Patent
Yen

(10) Patent No.: US 7,754,348 B2
(45) Date of Patent: Jul. 13, 2010

(54) PHENANTHROLINE COMPOUND AND ORGANIC LIGHT EMITTING DEVICE USING THE SAME

(75) Inventor: Feng Wen Yen, Hsin-Chu (TW)

(73) Assignee: Luminescene Technology Corp. (TW)

( * ) Notice: Subject to any disclaimer, the term of this patent is extended or adjusted under 35 U.S.C. 154(b) by 570 days.

(21) Appl. No.: 11/740,288

(22) Filed: Apr. 25, 2007

(65) Prior Publication Data

US 2008/0265746 A1    Oct. 30, 2008

(51) Int. Cl.
*H01L 51/54* (2006.01)
*H01J 1/63* (2006.01)
*C07D 471/04* (2006.01)

(52) U.S. Cl. .................. 428/690; 428/917; 313/504; 313/506; 546/88

(58) Field of Classification Search .................. None
See application file for complete search history.

(56) References Cited

U.S. PATENT DOCUMENTS

2006/0097227 A1    3/2006  Okajima

FOREIGN PATENT DOCUMENTS

EP    1097980 A2 *   5/2001
EP    1097980 A3     9/2003

* cited by examiner

*Primary Examiner*—Dawn L Garrett
(74) *Attorney, Agent, or Firm*—Hamre, Schumann, Mueller & Larson, P.C.

(57) ABSTRACT

The present invention discloses a phenanthroline compound which can be used as electron-transporting material in organic electroluminescence devices is disclosed. The mentioned phenanthroline compound is represented by the following.

formula(I)

-continued

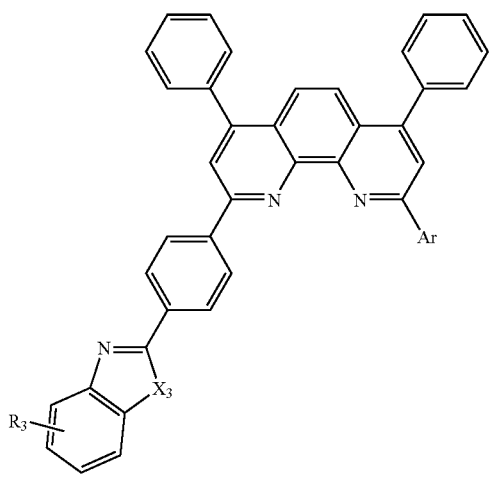

formula(II)

wherein Ar is selected from the group consisting of hydrogen atom, alkyl, aryl, wherein $R_1$, $R_2$ and $R_3$ are identical or different. $R_1$, $R_2$ and $R_3$ are independently selected from the group consisting of hydrogen atom, alkyl, halide, wherein $X_1$, $X_2$ and $X_3$ are identical or different. $X_1$, $X_2$ and $X_3$ are independently selected from the atom or group consisting of O, S, N—$R_4$ and $R_4$ is selected from the group consisting of hydrogen atom, alkyl, aryl.

15 Claims, 1 Drawing Sheet

PHENANTHROLINE COMPOUND AND ORGANIC LIGHT EMITTING DEVICE USING THE SAME

BACKGROUND OF THE INVENTION

1. Field of the Invention

The present invention is generally related to phenanthroline compound and organic light emitting device using the compound. More specifically, the present invention related to phenanthroline compound having general formula (I) and formula (II), an organic light emitting device employing phenanthroline compound as electron transporting layer can lower driving voltage, prolong half-lifetime and increasing efficiency.

2. Description of the Prior Art

Organic light-emitting devices (OLEDs) have received much attention due to their potential applications to flat panel displays. OLEDs are generally composed of functionally divided organic multi-layers, e.g., hole transporting layer (HTL), emissive layer (EML), and electron transporting layer (ETL), and so on. A electron transporting material (ETM) have good charge carrier mobility and excellent operational durability can lower driving voltage and power consumption, increasing efficiency and half-lifetime of OLEDs. There are many kinds of ETM had been widely used for OLEDs, such as metal chelates ($Alq_3$), benzimidazle, oxadiazole, Bipyridine-oxadiazole, triazes and phenanthrolines derivatives, and so on. Phenanthroline derivatives are well-know used for OLEDs such as bathophenanthroline (Bphen), 2,9-dimethyl-4,7-diphenyl-1,10-phenanthroline (BCP). But conventional phenanthroline derivatives exhibit lower Tg (Bphen=55° C., BCP=65° C.), lower heat-resistant ($T_d$: weight loss <0.5% at 240° C. for Bphen and 260° C. for BCP. It's difficult to operate under deposition process and its OLEDs show lower stability and short half-lifetime.

Many works had modified phenanthroline chemical structure such as EP1097980A3 claim bathophenanthroline compound that introduce alkyl group and aryl group into 2,9-position of bathophenanthroline. US 2006/0097227 A1 claim phenanthroline compound that introduce fluorenyl group, fluoranthenyl group, perylenyl group into 2,9-position and 4,7-position of phenanthroline. But these electron-transporting materials (phenanthroline derivatives) are still needed corresponding to increase thermal stability and practical operation durability. Especially the half-lifetime and driving voltage needed to be improved for the purpose of industry practice.

SUMMARY OF THE INVENTION

In accordance with the present invention, new phenanthroline compounds and their use for electron transporting layer of OLEDS are provided. These new phenanthroline compounds can overcome the drawbacks of the mentioned conventional materials. In order to obtain better thermal stability and increasing its charge carrier mobility, we introduced benzimidazole, benzothiazole, benzoxazole group into 2,9-position moiety of phenanthroline compound, so as to enlargement of molecular size, enhances the stability of the amorphous glassy state and increasing its charge carrier mobility.

An object of the present invention is to improve the Tg and heat-resistant physical characteristic (higher $T_d$) of new phenanthroline compound.

Another object of the present invention is to apply these new phenanthroline compounds for electron transporting layer of OLEDs and improve the half-lifetime, lower driving voltage, lower power consumption and increase the efficiency.

The present invention has the economic advantages for industrial practice. Accordingly, the present invention discloses a new phenanthroline compound which can be used for OLEDs is disclosed. The mentioned new phenanthroline compound is represented by the following formula (I) and formula (II):

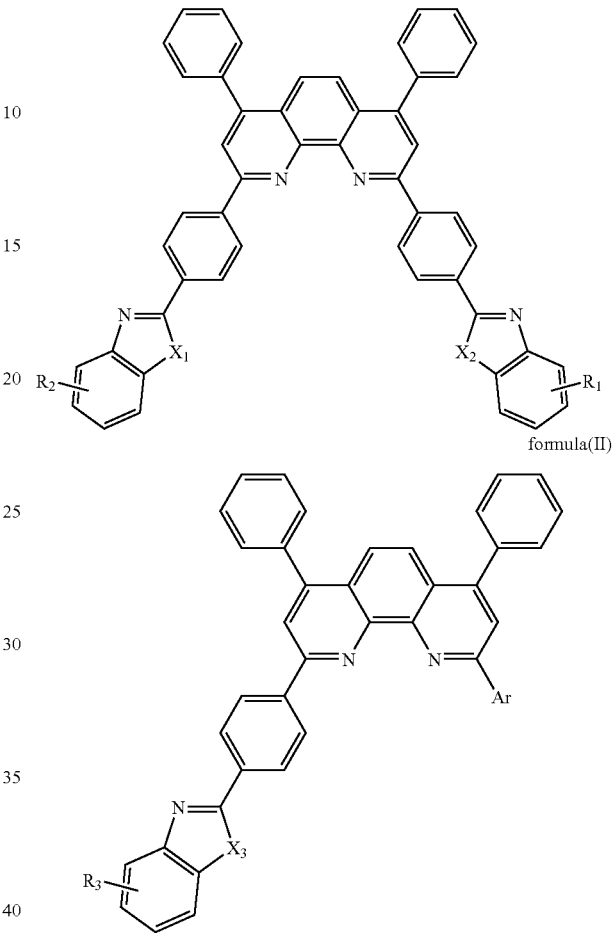

Ar is selected from the group consisting of hydrogen atom, alkyl, aryl, wherein $R_1$, $R_2$ and $R_3$ are identical or different, and $R_1$, $R_2$ and $R_3$ are independently selected from the group consisting of hydrogen atom, alkyl, halide. Wherein $X_1$, $X_2$ and $X_3$ are identical or different, and $X_1$, $X_2$ and $X_3$ are independently selected from the atom or group consisting of O, S, N—$R_4$ and $R_4$ is selected from the group consisting of hydrogen atom, alkyl, aryl.

DESCRIPTION OF THE PREFERRED EMBODIMENTS

Figure 1:
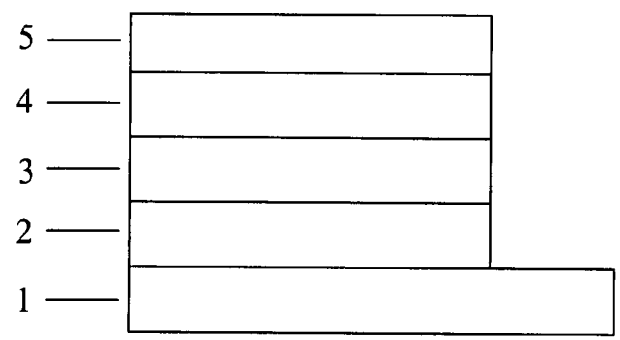
FIG. 1 show an example of organic light emitting device in the present invention. 1 is transparent electrode, 5 is metal electrode, 2 is hole transporting layer which is deposited onto 1, 3 is emitting layer which is deposited onto 2, 4 is electron transporting layer which is deposited onto 3.
Figure 2:
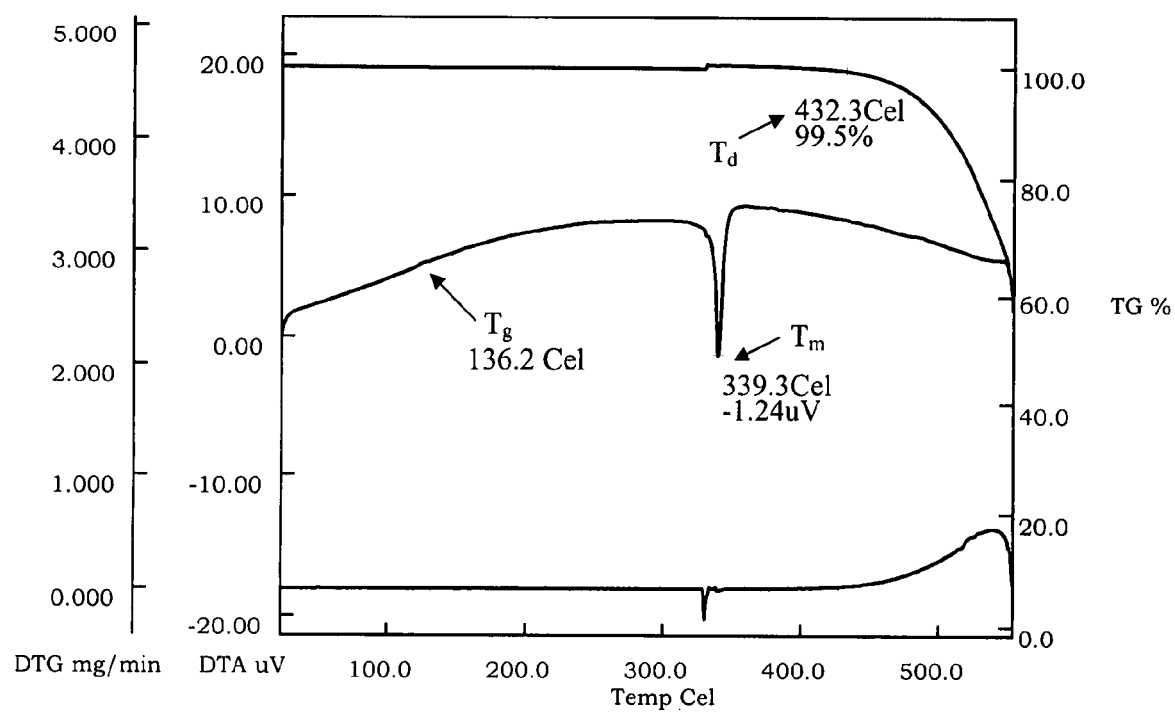
FIG. 2 show an example of phenanthroline compound in the present invention for its $T_g$, $T_d$ and $T_m$.

What probed into the invention is new phenanthroline compound and organic light emitting device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Definition

The term "thermal degradation temperature ($T_d$)" herein refers to the temperature when the weight loss of a heated specimen being 0.5 wt %. "$T_g$" herein refers to the glass transition temperature and "$T_m$" herein refers to Melting point.

In a first embodiment of the present invention, new phenanthroline compound which can be used as electron transporting layer of OLEDs is disclosed. The mentioned new phenanthroline compound is represented by following formula (I) and formula (II):

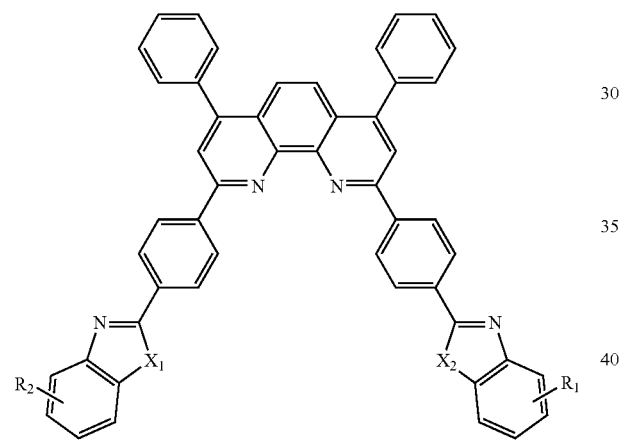

Ar is selected from the group consisting of hydrogen atom, alkyl, aryl, wherein $R_1$, $R_2$ and $R_3$ are identical or different, and $R_1$, $R_2$ and $R_3$ are independently selected from the group consisting of hydrogen atom, alkyl, halide. Wherein $X_1$, $X_2$ and $X_3$ are identical or different, and $X_1$, $X_2$ and $X_3$ are independently selected from the atom or group consisting of O, S, N—$R_4$ and $R_4$ is selected from the group consisting of hydrogen atom, alkyl, aryl.

In this embodiment, some phenanthroline compounds are listed in Table 1.

TABLE 1

| | Structure formula |
|---|---|
| Compound 1 | |

TABLE 1-continued
Structure formula
Compound 2
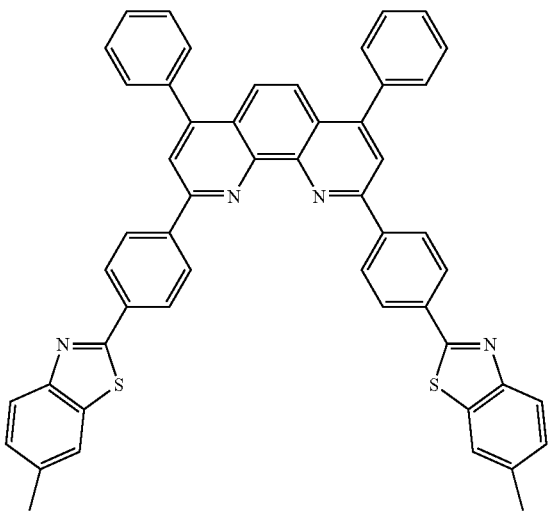
Compound 3
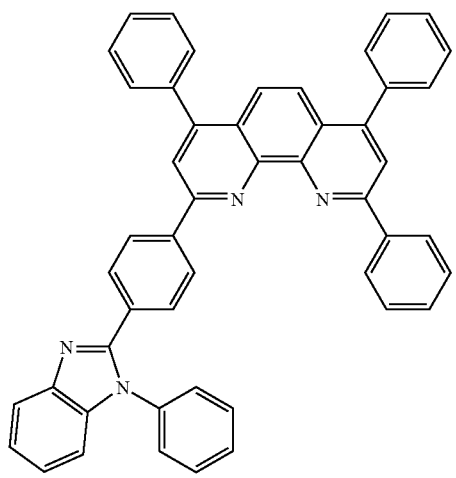
Compound 4
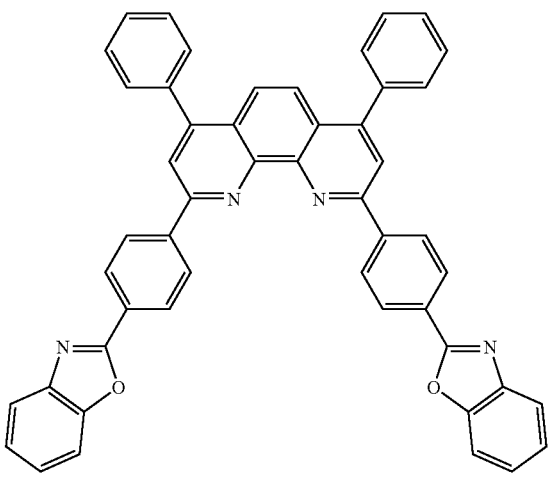

TABLE 1-continued
| | Structure formula |
|---|---|
| Compound 5 | 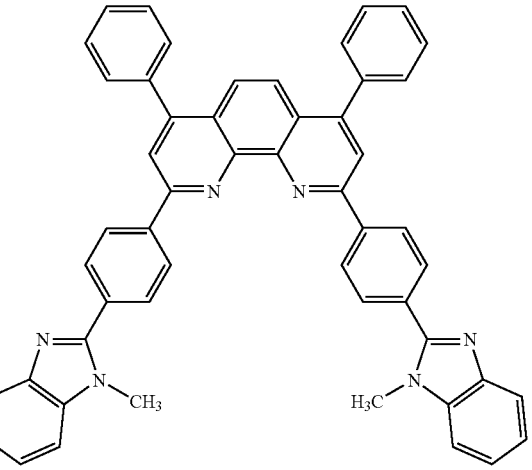 |
| Comparable Example 1 | 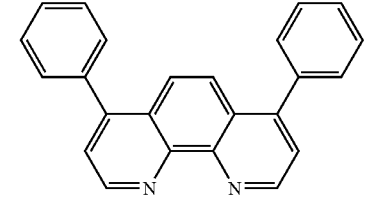 |
| Comparable Example 2 | 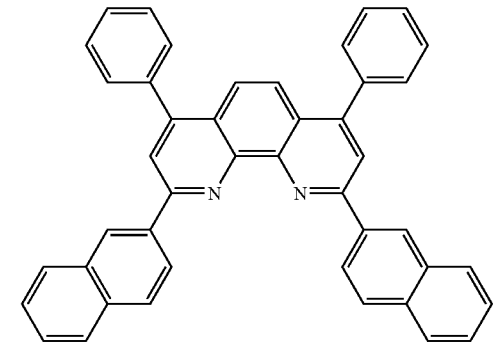 |
| Comparable Example 3 | 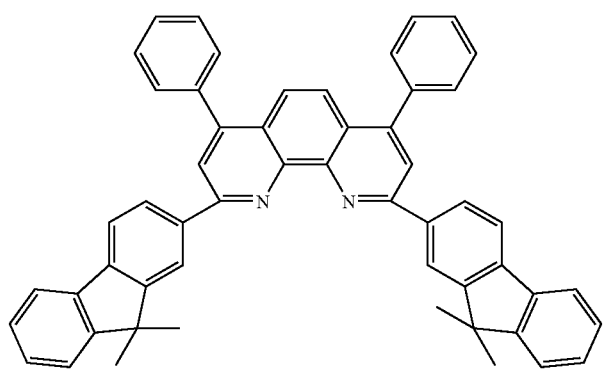 |

Synthesis of Compound 1~5 and Comparable Example 2~3

General synthesis gateway can be is represented by the following scheme (I):

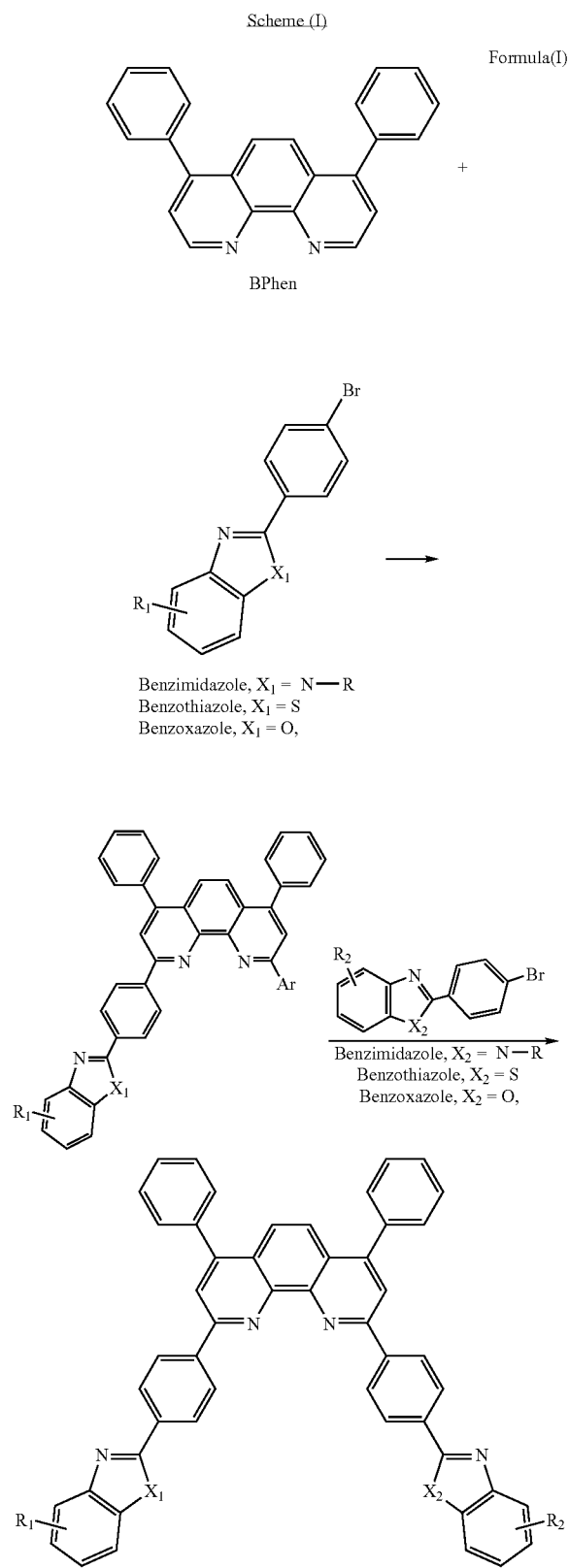

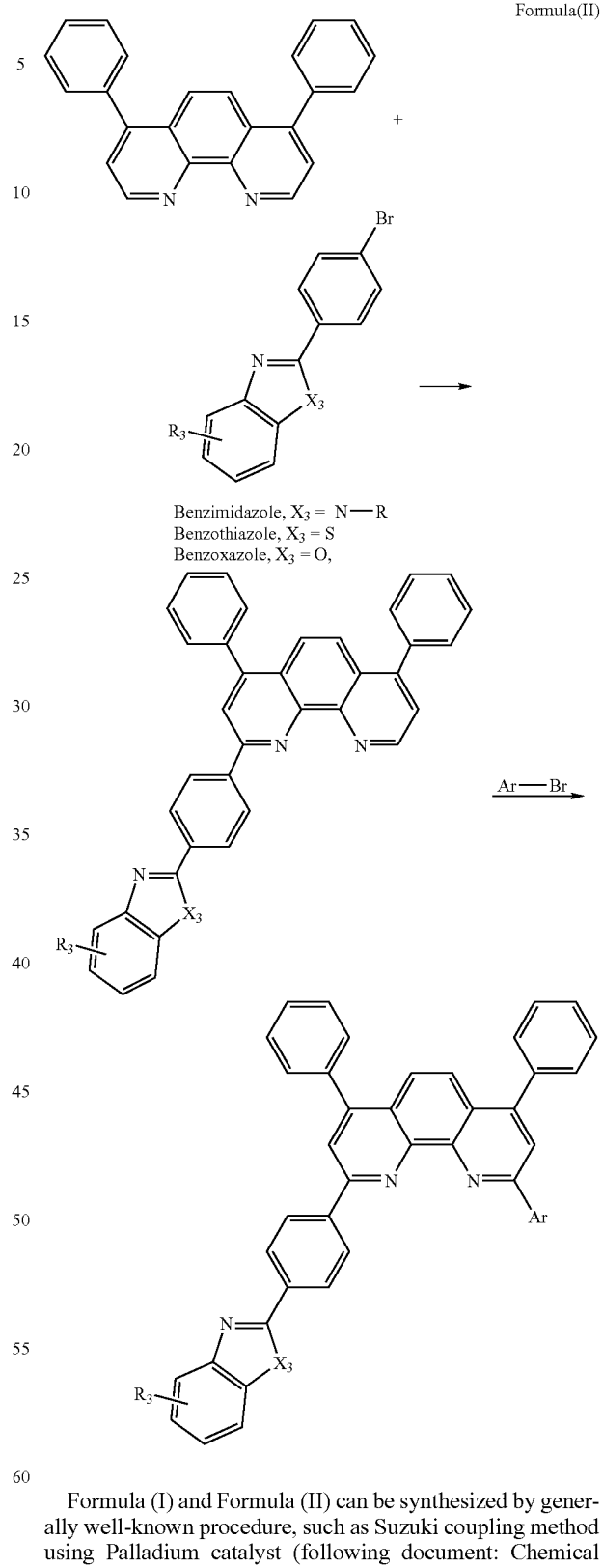

Formula (I) and Formula (II) can be synthesized by generally well-known procedure, such as Suzuki coupling method using Palladium catalyst (following document: Chemical Review 1995, 95, 2457~2483) react with starting material bathophenanthroline (BPhen) which can be brought from Sigma-Aldrish (CAS No: 1662-01-7), and benzimidazole, benzothiazole, benzoxazole group can be synthesized by fol-

EXAMPLE 1

Synthesis of Compound 1

Synthesis of 2-(4-bromophenyl)benzo[d]thiazole 2-aminothiophenol 9.01 g (72 mmole), 4-bromobenzaldehyde 16 g (87 mmole), and 2.8 g of PTSA (14 mmole) was stirred in 150 ml of Toluene, the reaction mixture was then heated to reflux for 16 hours, after cooling, the reaction mixture was extracted with water, and then the organic layer was evaporated to dry, the residue was then recrystallized with acetone to get 13.43 g of product (yield=64.3%).

Synthesis of 2-(4-(benzo[d]thiazol-2-yl)phenyl)-4,7-diphenyl-1,10-phenanthroline To a three-necked flask of 250 ml, 1.63 g (5.6 mmol) of 2-(4-bromophenyl)benzo[d]thiazole and 70 ml of THF were charged, then 3.5 ml (5.6 mmol) n-butyllithium (1.6M in Hexane solution) was dropped under stirring at −78° C. in a nitrogen atmosphere. The mixture was stirred for one hour at −78° C., and a solution of 1.86 g (5.6 mmol) 4,7-diphenyl-1,10-phenanthroline in 30 ml THF was dropped. Then the mixture was stirred at room temperature for overnight and was added with water. The organic layer was extracted with Dichloromethane and dried with anhydrous magnesium sulfate, the solvent was removed by rotary evaporation. The product was purified by column chromatography on alumina using Dichloromethane/Hexane as eluent and dried in vacuo, obtaining white powder compound 1.27 g (yield of 41.91%), MS (m/z, FAB$^+$) 541.6.

EXAMPLE 2

Synthesis of Compound 2

Synthesis of 2-(4-bromophenyl)-6-methylbenzo[d]thiazole 2-amino-5-methylthiophenol 10.02 g (72 mmole), 4-bromobenzaldehyde 16 g (87 mmole), and 2.8 g of PTSA (14 mmole) was stirred in 150 ml of Toluene, the reaction mixture was then heated to reflux for 16 hours, after cooling, the reaction mixture was extracted with water, and then the organic layer was evaporated to dry, the residue was then recrystallized with acetone to get 16.85 g of product (yield=76.94%).

Synthesis of 2,9-bis(4-(6-methylbenzo[d]thiazol-2-yl)phenyl)-4,7-diphenyl-1,10-phenanthroline To a three-necked flask of 250 ml, 6.69 g (22 mmol) of 2-(4-bromophenyl)6-methylbenzo[d]thiazole and 70 ml of THF were charged, then 13.8 ml (22 mmol) n-butyllithium (1.6M in Hexane solution) was dropped under stirring at −78° C. in a nitrogen atmosphere. The mixture was stirred for one hour at −78° C., and a solution of 1.86 g (5.6 mmol) 4,7-diphenyl-1,10-phenanthroline in 30 ml THF was dropped. Then the mixture was stirred at room temperature for overnight and was added with water. The organic layer was extracted with Dichloromethane and dried with anhydrous magnesium sulfate, the solvent was removed by rotary evaporation. The product was purified by column chromatography on alumina using Dichloromethane/Hexane as eluent and dried in vacuo, obtaining white powder compound 2.24 g (yield of 51.37%). MS (m/z, FAB$^+$) 778.9 (100%).

EXAMPLE 3

Synthesis of Compound 3

Synthesis of 2-(4-bromophenyl)-1-phenyl-1H-benzo[d]imidazole

N-Phenyl-o-phenylenediamine 13.27 g (72 mmole), 4-bromobenzaldehyde 16 g (87 mmole), and 2.8 g of PTSA (14 mmole) was stirred in 150 ml of Toluene, the reaction mixture was then heated to reflux for 16 hours, after cooling, the reaction mixture was extracted with water, and then the organic layer was evaporated to dry, the residue was then recrystallized with acetone to get 14.51 g of product (yield=57.71%).

Synthesis of 2,4,7-triphenyl-1,10-phenanthroline

To a three-necked flask of 250 ml, 0.97 g (6.16 mmol) of bromobenzene and 70 ml of THF were charged, then 3.9 ml (22 mmol) n-butyllithium (1.6M in Hexane solution) was dropped under stirring at −78° C. in a nitrogen atmosphere. The mixture was stirred for one hour at −78° C., and a solution of 1.86 g (5.6 mmol) 4,7-diphenyl-1,10-phenanthroline in 30 ml THF was dropped. Then the mixture was stirred at room temperature for overnight and was added with water. The organic layer was extracted with Dichloromethane and dried with anhydrous magnesium sulfate, the solvent was removed by rotary evaporation. The product was purified by column chromatography on alumina using Dichloromethane/Hexane as eluent and dried in vacuo, obtaining white powder compound 0.85 g (yield of 37.21%).

Synthesis of 2,4,7-triphenyl-9-(4-(1-phenyl-1H-benzo[d]imidazol-2-yl)phenyl)-1,10-phenanthroline To a three-necked flask of 250 ml, 3.84 g (11 mmol) of 2-(4-bromophenyl)-1-phenyl-1H-benzo[d]imidazole and 70 ml of THF were charged, then 6.9 ml (11 mmol) n-butyllithium (1.6M in Hexane solution) was dropped under stirring at −78° C. in a nitrogen atmosphere. The mixture was stirred for one hour at −78° C., and a solution of 2.29 g (5.6 mmol) 2,4,7-triphenyl-1,10-phenanthroline in 30 ml THF was dropped. Then the mixture was stirred at room temperature for overnight and was added with water. The organic layer was extracted with Dichloromethane and dried with anhydrous magnesium sulfate, the solvent was removed by rotary evaporation. The product was purified by column chromatography on alumina using Dichloromethane/Hexane as eluent and dried in vacuo, obtaining white powder compound 1.78 g (yield of 47.12%). MS (m/z, FAB$^+$) 676.8(100%).

EXAMPLE 4

Synthesis of Compound 4

Synthesis of 2-(4-bromophenyl)benzo[d]oxazole 2-aminophenol 7.86 g (72 mmole), 4-bromobenzaldehyde 16 g (87 mmole), and 2.8 g of PTSA (14 mmole) was stirred in 150 ml of Toluene, the reaction mixture was then heated to reflux for 16 hours, after cooling, the reaction mixture was extracted with water, and then the organic layer was evaporated to dry, the residue was then recrystallized with acetone to get 12.85 g of product (yield=65.12%).

Synthesis of 2,9-bis(4-(benzo[d]oxazol-2-yl)phenyl)-4,7-diphenyl-1,10-phenanthroline To a three-necked flask of 250 ml, 6.03 g (22 mmol) of 2-(4-bromophenyl)benzo[d]oxazole and 70 ml of THF were charged, then 13.8 ml (22 mmol) n-butyllithium (1.6M in Hexane solution) was dropped under stirring at −78° C. in a nitrogen atmosphere. The mixture was stirred for one hour at −78° C., and a solution of 1.86 g (5.6 mmol) of 4,7-diphenyl-1,10-phenanthroline in 30 ml THF was dropped. Then the mixture was stirred at room temperature for overnight and was added with water. The organic layer was extracted with Dichloromathane and dried with anhydrous magnesium sulfate, the solvent was removed by rotary evaporation. The product was purified by column chromatography on alumina using Dichloromethane/Hexane as eluent and dried in vacuo, obtaining white powder compound 2.10 g (yield of 52.14%). MS (m/z, FAB$^+$) 718.8.

EXAMPLE 5

Synthesis of Compound 5

Synthesis of 2-(4-bromophenyl)-1H-benzo[d]imidazole o-Phenylenediamine 7.79 g (72 mmole), 4-bromobenzaldehyde 16 g (87 mmole), and 2.8 g of PTSA (14 mmole) was stirred in 150 ml of Toluene, the reaction mixture was then heated to reflux for 16 hours, after cooling, the reaction mixture was extracted with water, and then the organic layer was evaporated to dry, the residue was then recrystallized with acetone to get 12.69 g of product (yield=64.54%).

Synthesis of 2-(4-bromophenyl)-1-methyl-1H-benzo[d]imidazole 12.69 g (46 mmole) of 2-(4-bromophenyl)-1H-benzo[d]imidazole, 3.17 g of K2CO3 (23 mmole), 120 ml of DMF, and 11.6 ml of dimethyl carbonate (138 mmole) were mixed together and heat to reflux. The reaction was completed in 3.5 hours. The reaction mixture was cooled to 3° C., and 250 ml of ice cold water was slowly added, The precipitated was filtered, and wash with 3*50 ml of water, this wet cake was dried under vacuum to get 9.96 g of product (yield=75.44%).

Synthesis of 2,9-bis(4-(1-methyl-1H-benzo[d]imidazol-2-yl)phenyl)-4,7-diphenyl-1,10-phenanthroline To a three-necked flask of 250 ml, 6.32 g (22 mmol) 2-bromonaphthalene and 70 ml of THF were charged, then 13.8 ml (22 mmol) n-butyllithium (1.6M in Hexane solution) was dropped under stirring at −78° C. in a nitrogen atmosphere. The mixture was stirred for one hour at −78° C., and a solution of 1.86 g (5.6 mmol) of 4,7-diphenyl-1,10-phenanthroline in 30 ml THF was dropped. Then the mixture was stirred at room temperature for overnight and was added with water. The organic layer was extracted with Dichloromethane and dried with anhydrous magnesium sulfate, the solvent was removed by rotary evaporation. The product was purified by column chromatography on alumina using Dichloromethane/Hexane as eluent and dried in vacuo, obtaining white powder compound 2.03 g (yield of 48.67%). MS (m/z, FAB$^+$) 744.8.

EXAMPLE 6

Synthesis of Comparable Example 2

Synthesis of 2,9-di(naphthalen-2-yl)-4,7-diphenyl-1,10-phenanthroline

To a three-necked flask of 250 ml, 4.56 g (22 mmol) of 2-bromonaphthalene and 70 ml of THF were charged, then 13.8 ml (22 mmol) n-butyllithium (1.6M in Hexane solution) was dropped under stirring at −78° C. in a nitrogen atmosphere. The mixture was stirred for one hour at −78° C., and a solution of 1.86 g (5.6 mmol) 4,7-diphenyl-1,10-phenanthroline in 30 ml THF was dropped. Then the mixture was stirred at room temperature for overnight and was added with water. The organic layer was extracted with Dichloromethane and dried with anhydrous magnesium sulfate, the solvent was removed by rotary evaporation. The product was purified by column chromatography on alumina using Dichloromethane/Hexane as eluent and dried in vacuo, obtaining white powder compound 1.79 g (yield of 54.56%). MS (m/z, FAB$^+$) 584.7.

EXAMPLE 7

Synthesis of Comparable Example 3

Synthesis of 2,9-bis(9,9-dimethyl-9H-fluoren-2-yl)-4,7-diphenyl-1,10-phenanthroline To a three-necked flask of 250 ml, 6.01 g (22 mmol) of 2-bromonaphthalene and 70 ml of THF were charged, then 13.8 ml (22 mmol) n-butyllithium (1.6M in Hexane solution) was dropped under stirring at −78° C. in a nitrogen atmosphere. The mixture was stirred for one hour at −78° C., and a solution of 1.86 g (5.6 mmol) 4,7-diphenyl-1,10-phenanthroline in 30 ml THF was dropped. Then the mixture was stirred at room temperature for overnight and was added with water. The organic layer was extracted with Dichloromethane and dried with anhydrous magnesium sulfate, the solvent was removed by rotary evaporation. The product was purified by column chromatography on alumina using Dichloromethane/Hexane as eluent and dried in vacuo, obtaining white powder compound 2.30 g (yield of 57.22%). MS (m/z, FAB$^+$) 716.9.

General Method of Producing Oleds

ITO-coated glasses with 15Ω☐$^{-1}$ and 1500 μm in thickness are provided (purchased from Sanyo vacuum, hereinafter ITO substrate) and cleaned in a number of cleaning steps in an ultrasonic bath (e.g. detergent, deionized water). Before vapor deposition of the organic layers, cleaned ITO substrates are further treated by UV and ozone.

These organic layers are applied onto the ITO substrate in order by vapor deposition in a high-vacuum unit (10$^{-6}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a guest material. This is achieved by co-vaporization from two or more sources. N,N'-Bis(naphthalene-1-yl)-N,N'-bis(phenyl)-benzidine (NPB) is most widely used as the hole transporting layer and Tris-(8-hydroxyquinoline) aluminum (Alq$_3$) is most widely used as the electron transporting/light emitting layer in OLEDs for its high thermal stability and good film forming property. It is reported that the thermal degradation temperature ($T_d$) of $Alq_3$ is about 303° C. 2,3,6,7-Tetrahydro-1,1,7-tetramethyl-1H,5H,11H-10-(2-benzo-thiazolyl)quinolizino-[9,9a, 1 gh]coum arin (C545T) is widely used as the green guest to co-vaporization with host ($Alq_3$) for green emissive layer.

A typical OLED consists of low work function metals, such as Al, Mg, Ca, Li and K, as the cathode by thermal evaporation, and the low work function metals can help electrons injecting the electron transporting layer from cathode. In addition, for reducing the electron injection barrier and improving the OLED performance, a thin-film electron injecting layer is introduced between the cathode and the electron transporting layer. Conventional materials of electron injecting layer are metal halide or metal oxide with low work function, such as LiF, MgO, or $Li_2O$.

On the other hand, after the OLEDs are fabricated, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 20° C.) and under atmospheric pressure.

EXAMPLE 8

Using a procedure analogous to the abovementioned general method, green-emitting OLEDs having the following device structure were produced: ITO/NPB(600 Å)/$Alq_3$ doped 2% C545T(350 Å)/electron transporting layer (200 Å)/LiF(5 Å)/Al(1200 Å). The I-V-B and half-life time of green device testing report as Table 2:

TABLE 2

| electron transporting layer | Voltage (V) | Luminance (cd/m$^2$) | Yield (cd/A) | Half-lifetime (hour) Initial luminance = 3000 (cd/m$^2$) |
|---|---|---|---|---|
| Compound 1 | 5 | 727 | 8.5 | 167 |
| Compound 2 | 5 | 1218 | 12.8 | 220 |
| Compound 3 | 5 | 782 | 7.1 | 195 |
| Compound 4 | 5 | 1153 | 12.1 | 176 |
| Compound 5 | 5 | 1333 | 11.6 | 238 |
| Comparable example 1 | 5 | 663 | 7.1 | 32 |
| Comparable example 2 | 5 | 850 | 11.5 | 50 |
| Comparable example 3 | 5 | 913 | 8.1 | 134 |
| $Alq_3$ | 5 | 525 | 11.0 | 125 |

In the above preferred embodiments, we show that new phenanthroline compounds have efficient electron transporting properties than comparable example 1~3 and $Alq_3$ with higher half-life time and practical operation durability. High luminance than comparable example 1~3 and $Alq_3$ has also been achieved at a driving voltage of 5V using the mentioned new phenanthroline compounds for green-emitting organic electroluminescent devices.

To sum up, the present invention discloses a new phenanthroline compound which can be used as electron-transporting material in organic electroluminescence devices is disclosed. The mentioned new phenanthroline compound is represented by the following formula (I) and formula (II):

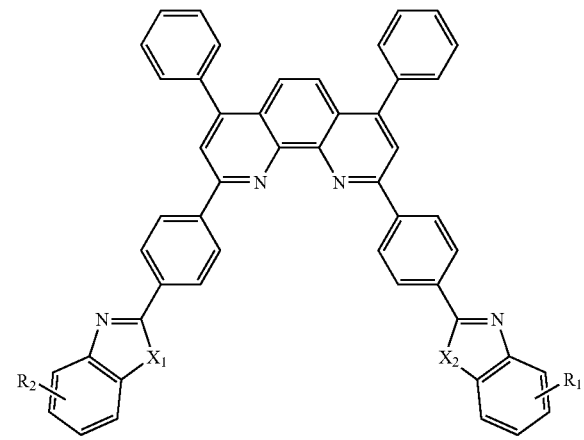

formula(I)

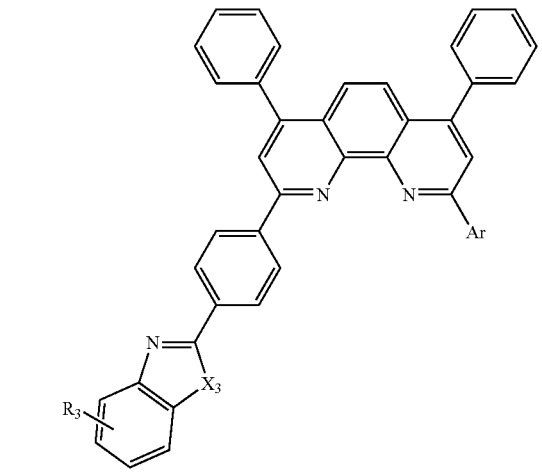

formula(II)

Ar is selected from the group consisting of hydrogen atom, alkyl, aryl, wherein $R_1$, $R_2$ and $R_3$ are identical or different. $R_1$, $R_2$ and $R_3$ are independently selected from the group consisting of hydrogen atom, alkyl, halide, wherein $X_1$, $X_2$ and $X_3$ are identical or different, and $X_1$, $X_2$ and $X_3$ are independently selected from the atom or group consisting of O, S, N—$R_4$ and $R_4$ is selected from the group consisting of hydrogen atom, alkyl, aryl.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A phenanthroline compound with a general formula (I) or general formula (II) as following:

formula(I)

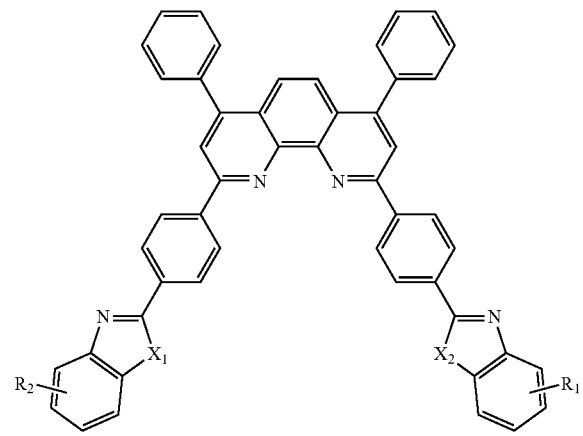

formula(II)

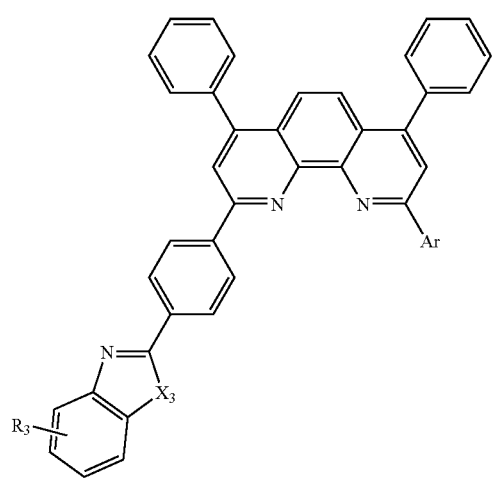

wherein Ar is selected from the group consisting of hydrogen atom, alkyl, and aryl, wherein $R_1$, $R_2$ and $R_3$ are identical or different, $R_1$, $R_2$ and $R_3$ are independently selected from the group consisting of hydrogen atom, alkyl, and halide wherein $X_1$, $X_2$ and $X_3$ are identical or different, $X_1$, $X_2$ and $X_3$ are independently selected from the atom or group consisting of O, S and N—$R_4$ and $R_4$ is selected from the group consisting of hydrogen atom, alkyl, and aryl.

2. The compound as claimed in claim 1, wherein each of $X_1$, $X_2$ and $X_3$ is S atom, each of $R_1$, $R_2$ and $R_3$ independently is alkyl and Ar is aryl.

3. The compound as claimed in claim 2, wherein said phenanthroline compound is:

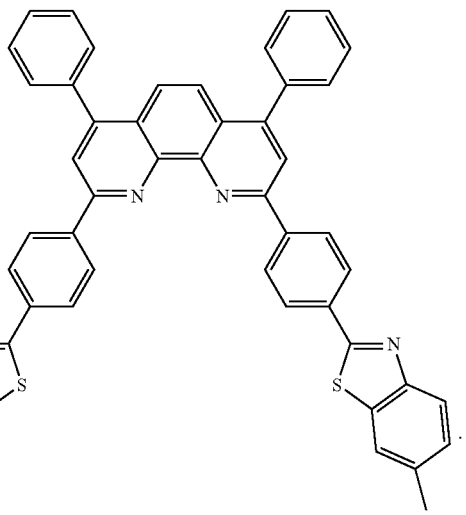

4. The compound as claimed in claim 1, wherein each of $X_1$, $X_2$ and $X_3$ is O atom, each of $R_1$, $R_2$ and $R_3$, independently is alkyl and Ar is aryl.

5. The compound as claimed in claim 4, wherein said phenanthroline compound is:

6. The compound as claimed in claim 1, wherein each of $X_1$, $X_2$ and $X_3$ is N—$R_4$, $R_4$ is aryl, each of $R_1$, $R_2$ and $R_3$ independently is alkyl and Ar is aryl.

7. The compound as claimed in claim 6, wherein said phenanthroline compound is:

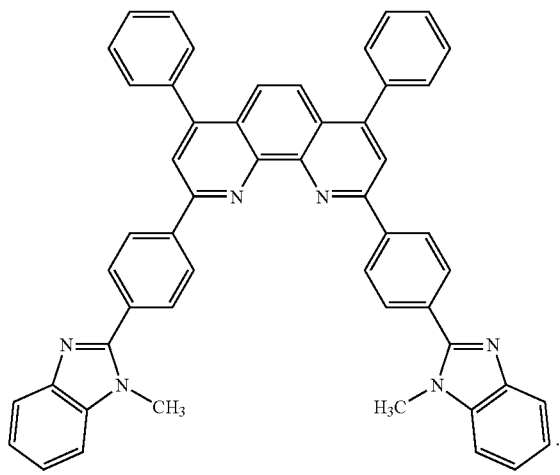

8. A organic light emitting device comprising a pair of electrodes consisting of a cathode and an anode and between the pairs of electrodes comprising a layer of phenanthroline compound represented as the following general formula (I) or general formula (II):

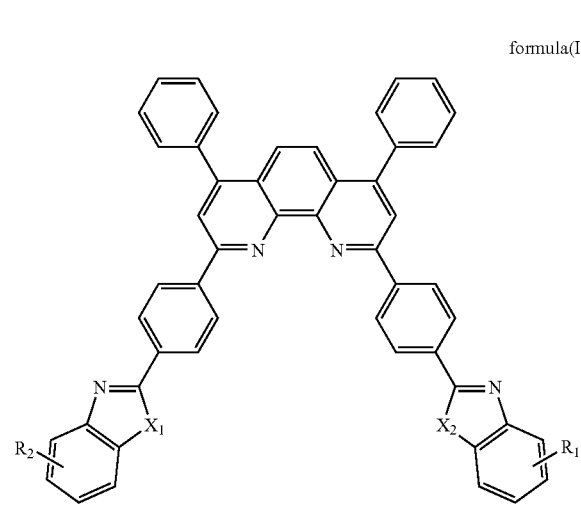

formula(I)

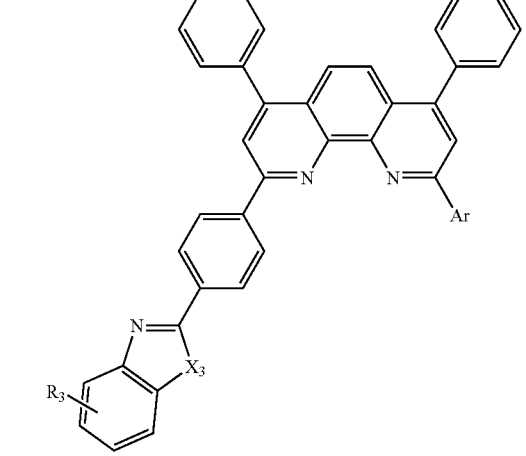

formula(II)

wherein Ar is selected from the group consisting of hydrogen atom, alkyl, and aryl, wherein $R_1$, $R_2$ and $R_3$ are identical or different, and $R_1$, $R_2$ and $R_3$ are independently selected from the group consisting of hydrogen atom, alkyl, and halide, wherein $X_1$, $X_2$ and $X_3$ are identical or different, $X_1$, $X_2$ and $X_3$ are independently selected from the atom or group consisting of O, S and N—$R_4$ and $R_4$ is selected from the group consisting of hydrogen atom, alkyl, and aryl.

9. The organic light emitting device as claimed in claim 8, wherein each of $X_1$, $X_2$ and $X_3$ is S atom, each of $R_1$, $R_2$ and $R_3$ independently is alkyl and Ar is aryl.

10. The organic light emitting device as claimed in claim 9, wherein said phenanthroline compound is:

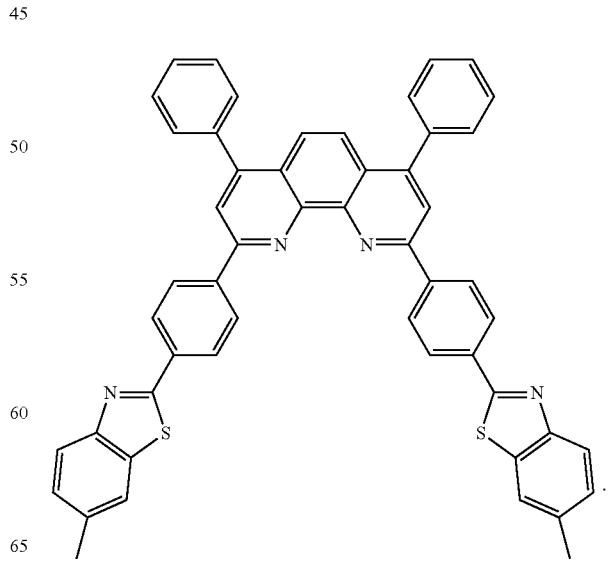

11. The organic light emitting device as claimed in claim 8, wherein each of $X_1$, $X_2$ and $X_3$ is O atom, each of $R_1$, $R_2$ and $R_3$ independently is alkyl and Ar is aryl.

12. The organic light emitting device as claimed in claim 11, wherein said phenanthroline compound is:

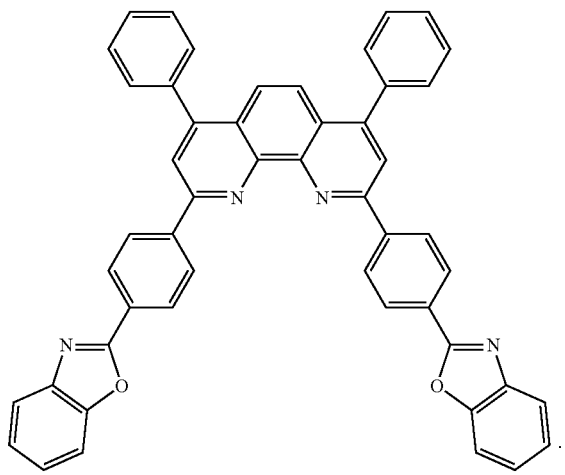

13. The organic light emitting device as claimed in claim 8, wherein each of $X_1$, $X_2$ and $X_3$ is N—$R_4$, $R_4$ is aryl, each of $R_1$, $R_2$ and $R_3$ independently is alkyl and Ar is aryl.

14. The organic light emitting device as claimed in claim 13, wherein said phenanthroline compound is:

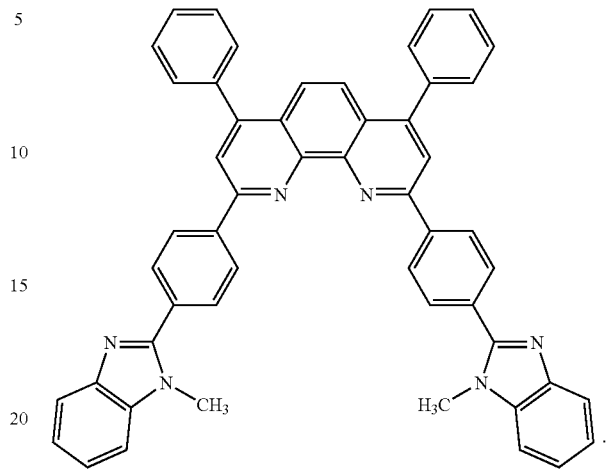

15. According to claim 8, an organic light emitting device comprising a layer of a phenanthroline compound represented as general formula (I) or general formula (II), which functions as electron transporting material of a light emitting layer.

* * * * *